United States Patent [19]

Chupp

[11] 4,322,553

[45] Mar. 30, 1982

[54] PROCESS FOR PRODUCING N-(HALOMETHYL)ACYLAMIDES

[75] Inventor: John P. Chupp, Kirkwood, Mo.

[73] Assignee: Monsanto Company, St. Louis, Mo.

[21] Appl. No.: 230,576

[22] Filed: Feb. 2, 1981

[51] Int. Cl.³ .............................................. C07C 102/00
[52] U.S. Cl. .................................... 564/209; 564/166; 564/170; 564/182; 564/189; 564/191; 564/193; 564/201; 564/202; 564/210; 564/211; 564/215; 564/218; 564/223; 564/224
[58] Field of Search ............... 564/166, 170, 182, 189, 564/191, 193, 194, 197, 201, 202, 215, 218, 223, 224, 209, 210, 211

[56] References Cited

U.S. PATENT DOCUMENTS 4,120,906 10/1978 Inamoto et al. ..................... 570/261

OTHER PUBLICATIONS

Martin et al., Chem. Abstracts, 84 (1976), #104601.
Wagner et al., Snythetic Organic Chem., John Wiley and Sons, N.Y., N.Y., 1953, p. 92.

Primary Examiner—Arthur P. Demers
Attorney, Agent, or Firm—William I. Andress; Howard C. Stanley

[57] ABSTRACT

The disclosure herein relates to a new process for the preparation of N-(halomethyl)acylamides by reacting the corresponding N-(alkoxymethyl)acylamide with thionyl chloride or thionyl bromide in the presence of a Lewis Acid catalyst.

28 Claims, No Drawings

PROCESS FOR PRODUCING N-(HALOMETHYL)ACYLAMIDES

BACKGROUND OF THE INVENTION

The invention herein pertains to the field of processes for the preparation of N-(halomethyl)acylamides particularly, N-(chloromethyl)-2-chloroacetamides.

DESCRIPTION OF THE PRIOR ART

N-(halomethyl)-2-haloacetamides generally are known in the prior art. These compounds are useful as herbicides themselves or as intermediates in the production of a wide variety of other N-methylene ether substituted 2-haloacetamides as disclosed, e.g., in U.S. Pat. Nos. 3,442,945, 3,630,716, 3,637,847, 3,574,746 and 3,586,496 and German Application No. 2,648,008. Other prior art N-methylene ether substituted 2-haloacetamides derived from the above N-(halomethyl) intermediates include those wherein the halogen atom of the N-(halomethyl) radical is replaced by alkoxy, polyalkoxy, aryl, heterocyclyl, etc., radicals.

The primary method disclosed in the prior art for producing N-(halomethyl)-2-haloacetamides involves the reaction of a primary aromatic amine with formaldehyde to produce the corresponding phenylazomethine which is then haloacetylated to obtain the desired N-halomethyl compound as disclosed, e.g., in said '716 and '847 patents.

Canadian Pat. No. 779,917 discloses alternative methods for producing N-(chloromethyl)-2-haloacetamides. In a first embodiment, a primary or secondary amine is reacted with formaldehyde to obtain the corresponding hexahydrotriazine which is then reacted with chloroacetyl chloride to obtain the corresponding N-(chloromethyl)-2-chloroacetamide. In a second procedure, a primary amine is reacted with chloroacetyl chloride, then with formaldehyde to produce the corresponding N-methylol-2-chloroacetamide, which, in turn, is reacted with phosphorus pentachloride to obtain the corresponding N-(chloromethyl)-2-chloroacetamide.

The above methods all possess limitations, thereby restricting access to these desirable intermediates. Thus, the addition of acid chlorides to monomeric or trimeric azomethines can be practically applied only when these latter materials are formed easily in high yields, necessitating electron-rich amines or anilines, in condensation with formaldehyde. Further, although the conversion of N-(hydroxymethyl)amides with phosphorus pentachloride, thionyl chloride or bromide or halogen acids can be convenient, this method is largely limited to substrates derived from reaction of formaldehyde with selected imides or amides wherein the methylol compound can be prepared; anilides and many other amides do not readily undergo such N-methylolation.

In order to develop a more general procedure to prepare N-(halomethyl)amides, advantage was taken of recent advances in amide N-alkylation, particularly under phase transfer conditions. The facile preparation of N-(alkoxymethyl)acylamides from secondary acylamides and halomethyl ethers can now be easily achieved, particularly for the more acidic substrates such as sec-anilide and 1-enamides; these and other N-(alkoxymethyl)amides unexpectedly provide the substrates for the new, general method for N-(halomethyl)amide formation described below.

To the knowledge of the inventor herein, it is unknown in the prior art to prepare N-(halomethyl) acylamides by the reaction of an N-methylene ether substituted-acylamide with thionyl chloride or bromide in the presence of a Lewis Acid catalyst as described in more detail below.

SUMMARY OF THE INVENTION

The invention herein relates to a process for preparing compounds of Formula I

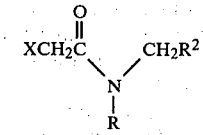

which comprises reacting a compound of Formula II

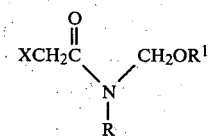

with thionyl chloride or thionyl bromide in the presence of a Lewis Acid catalyst where in the above formulae X is hydrogen, halogen, a $C_{1-6}$ alkyl or haloalkyl radical, a $C_{3-7}$ cycloalkyl radical, a phenyl or benzyl radical or any of said radicals optionally substituted with other radicals which are inert to a thionyl chloride, e.g., halogen, $NO_2$, $CF_3$, $C_{1-6}$ alkyl or alkoxy, phenyl or benzyl, etc.;

R is a $C_{1-20}$ alkyl radical, an acyclic 1-alken-1-yl radical having up to 10 carbon atoms, a cycloalkyl or 1-cycloalken-1-yl radical having up to 7 carbon atoms, a phenyl radical or said cycloalkyl, 1-cycloalken-1-yl or phenyl radicals substituted with one or more $C_{1-6}$ alkyl, alkoxy or alkoxyalkyl, $C_{2-4}$ alkenyl or $C_{3-4}$ alkenyloxy, $NO_2$ or $CF_3$ radicals or halogen;

$R^1$ is a hydrocarbyl radical having up to 10 carbon atoms or such radical substituted with halogen or $C_{1-8}$ alkoxy or alkoxyalkyl groups and $R^2$ is a chloro or bromo atom.

The process of this invention in preferred aspects is used to prepare compounds according to Formula I wherein X is chloro and R is a substituted phenyl radical as defined above.

The process of this invention is suitably conducted at room temperatures, but in preferred embodiments at reflux temperatures and, more broadly, within the range of 20° to 100° C.

Lewis Acids used to catalyze cleavage of the N-methylene ether group with thionyl chloride include sulfuric acid, hydrogen chloride, hydrofluoric acid, boron trifluoride, aluminum trichloride, etc. The preferred Lewis Acid herein is boron trifluoride etherate, $BF_3 \cdot O(C_2H_5)_2$.

The unique and unobvious character of the present invention is made manifest by reference to expected reactions which do not occur when N-(alkoxymethyl)acylamides are reacted with thionyl chloride according to this invention. For example, in starting N-(alkoxymethyl)-2-haloacetamides having alkoxy or alkoxyalkyl radicals substituted on the anilide ring, there are two ether linkages which could interchange with the reactant halide. However, according to the process of this invention, only the ether linkage in the N-methylene ether moiety is interchanged, leaving the anilide-substituted ether linkage intact. Although the reaction of alcohols with a thionyl halide to form alkyl halides is known, the reaction of such halides with ethers is not known; in fact, such reactions can only proceed with the use of Lewis Acids as first described herein.

An advantageous feature of the process of this invention is that thionyl chloride and thionyl bromide are scavengers of water, thus preventing hydrolysis of the final product to secondary anilide by water formed or present in the reaction.

Yet another advantage in the use of thionyl chloride or bromide herein is their transparency to hydrogen magnetic resonance ('Hmr) spectrometry, a convenient and occasionally necessary analytical technique for N-halomethyl amides, since gas-liquid chromatography temperatures often decompose this reagent type.

DETAILED DESCRIPTION OF THE INVENTION

EXAMPLE 1

This example illustrates an embodiment of the invention wherein the N-methylene ether radical of the substrate compound is cleaved by the catalytic action of the Lewis Acid hydrogen chloride generated in situ by the reaction of methanol and thionyl chloride ($SOCl_2$). Without the methanol present in this embodiment, thionyl chloride, although an electrophilic reagent, does not effect said ether cleavage.

Ten (10.0) g of 2',6'-diethyl-N-(methoxymethyl)-2-chloroacetanilide (common name "alachlor") when refluxed with 60 ml of $SOCl_2$ for periods from 12–24 hours gave little evidence of the formation of 2',6'-diethyl-N-(chloromethyl)-2-chloroacetanilide ("CMA"), the desired product.

The reaction mixture was cooled to room temperature and 1–2% methanol (0.3 ml) added; the mixture was permitted to stand about 12 hours. Nmr analysis revealed the presence of appreciable CMA, which did not increase upon heating. Upon standing for about three days at room temperature complete conversion of the starting material to CMA occurred.

In this embodiment, $SOCl_2$ reacts with the alcohol, methanol, to produce HCl which protonates the ether oxygen, catalyzing carbonium ion formation, thus inducing reaction with $SOCl_2$. Refluxing of this reaction mixture does not hasten the reaction, but, in fact, inhibits conversion of the starting material to CMA. This apparent anomaly, however, is explained on the basis of catalyst loss by facile HCl elimination by refluxing. Accordingly, in preferred embodiments, the process of this invention is more beneficially-conducted by using a non-volatile Lewis Acid catalyst which will not be eliminated during refluxing to enhance reaction rates, as illustrated by the use of $BF_3$.etherate in the examples below.

EXAMPLE 2

This example illustrates the preparation of CMA from alachlor as in Example 1 above, except a different acid catalyst system is used.

Alachlor (10.0 g) was dissolved in 60 ml of $SOCl_2$ containing 0.20 ml of $BF_3.O(C_2H_5)_2$. The mixture was refluxed six (6) hours, at which time Nmr analysis of the solution indicated complete conversion of alachlor to CMA. The $SOCl_2$ was stripped, toluene added and the mixture re-stripped under vacuum to give greater than 90% yield of CMA.

EXAMPLE 3

To 100 ml of $SOCl_2$ containing 4 drops of $BF_3.O(C_2H_5)_2$ was added 5.7 g of 2'-sec-butyl-6'-ethyl-N-(methoxymethyl)-2-chloroacetanilide and the mixture refluxed for one hour. The mixture was cooled to room temperature and the $SOCl_2$ stripped off. The residue was taken up in $CH_2Cl_2$ and washed with 37% HCl, then dried over $MgSO_4$. There was obtained 3.1 g (52% yield) of yellow oil, boiling at 122° C. at 0.1 mm Hg (Kugelrohr).

| Calc'd for $C_{15}H_{21}Cl_2NO$ (%): | | |
|---|---|---|
| Element | Theory | Found |
| C | 59.61 | 59.06 |
| H | 7.00 | 7.04 |
| Cl | 23.46 | 22.96 |

The product was identified as 2'-sec-butyl-6'-ethyl-N-(chloromethyl)-2-chloroacetanilide.

EXAMPLE 4

2'-(Trifluoromethyl)-6'-n-propyl-N-(methoxymethyl)-2-chloroacetanilide (6.6 g) was dissolved in 100 ml of $SOCl_2$ to which was added 4 drops of $BF_3.O(C_2H_5)_2$; the mixture was heated to reflux and held at that temperature for about 18 hours. The mixture was cooled to room temperature. Nmr showed complete reaction. The $SOCl_2$ was stripped, the residue taken up with hexane and then stripped again. Ether was added to the residue and washed with 10% HCl.

After layer separation, the organic layer was dried, filtered and stripped. Ether and hexane were added to the residue and after cooling, 5.5 g of a white solid (82% yield) was obtained. The product was identified as 2'-(trifluoromethyl)-6'-n-propyl-N-(chloromethyl)-2-chloroacetanilide.

EXAMPLE 5

2'-(trifluoromethyl)-6'-ethyl-N-(methoxymethyl)-2-chloroacetanilide, 14.8 g, was dissolved in 100 ml $SOCl_2$ and about 4 drops $BF_3.O(C_2H_5)_2$ added thereto. The temperature was raised to reflux and held there for about 24 hours. The $SOCl_2$ was stripped, $CH_2Cl_2$ added and the mixture vacuum stripped again. Additional $CH_2Cl_2$ was added and the mixture washed with 37% HCl, dried ($MgSO_4$), filtered and stripped. The residue was taken up in a hexane/ether solution and recrystallized to give 11.7 g (78% yield) of white solid, m.p. 46°–50° C.

| Anal. Cal'd for $C_{12}H_{12}Cl_2F_3NO$ (%) | | |
|---|---|---|
| Element | Theory | Found |
| C | 45.88 | 45.89 |
| H | 3.85 | 3.89 |
| N | 4.46 | 4.45 |

The product was identified as 2'-(trifluoromethyl)-6'-ethyl-N-(chloromethyl)-2-chloroacetanilide.

EXAMPLE 6

Following substantially the same procedure as described in Example 5, but substituting 2'-(trifluoromethyl)-6'-methyl-N-(methoxymethyl)-2-haloacetanilide as starting material, there is obtained the corresponding N-chloromethyl compound as a yellow oil $N_D^{25}$ 1.5076.

Anal. Cal'd for $C_{11}H_{10}Cl_2F_3NO$ (%)

| Element | Theory | Found |
|---------|--------|-------|
| C | 44.02 | 44.82 |
| H | 3.36 | 3.43 |
| N | 4.67 | 4.74 |

EXAMPLE 7

Similarly prepared as above is the compound 2'-trifluoromethyl)-N-(chloromethyl)-2-chloroacetanilide, while crystals, m.p. 63°–65° C.

Anal. Calc'd for $C_{10}H_8Cl_2F_3NO$(%)

| Element | Theory | Found |
|---------|--------|-------|
| C | 53.90 | 53.79 |
| H | 6.33 | 6.36 |
| Cl | 21.21 | 21.15 |
| N | 4.19 | 4.15 |

The advantageous feature of selectively cleaving the ether group on the amide nitrogen atom rather than on the anilide ring by the thionyl chloride with Lewis Acid catalyst is shown below in Examples 8–10.

EXAMPLE 8

2'-n-Butoxy-6'-ethyl-N-(methoxymethyl)-2-chloroacetanilide, 6.35 g., in 100 ml SOCl₂ containing 4 drops of BF₃.O(C₂H₅)₂ were refluxed for two hours. The SOCl₂ was stripped, then toluene added and the mixture again stripped. Additional toluene was added and the mixture washed with 10% HCl, dried over MgSO₄ and evaporated by Kugelrohr at 140°/0.1 mm Hg to give 4.6 g (72% yield) of yellow oil $N^{23.2}$ 1.5334.

Anal. calc'd for $C_{15}H_{21}Cl_2NO_2$(%):

| Element | Theory | Found |
|---------|--------|-------|
| C | 56.61 | 56.48 |
| H | 6.65 | 6.68 |
| Cl | 22.28 | 22.20 |
| N | 4.40 | 4.37 |

The product was identified as 2'-n-butoxy-6'-ethyl-N-(chloromethyl)-2-chloroacetanilide.

EXAMPLE 9

Five (5.0) g of 2'-isobutoxy-N-(methoxymethyl)-2-chloroacetanilide and 4 drops of BF₃.O(C₂H₅)₂ were added to 100 ml of SOCl₂ and the mixture heated at reflux temperature for 1.5 hours. The SOCl₂ was stripped off and toluene added, then stripped again to remove all SOCl₂. The residue was taken up in ether, washed with 10% HCl, dried and evaporated to give 5.0 g (86%) of a yellow oil, b.p.137° C. at 0.15 mm Hg (Kugelrohr).

Anal. Calc'd for $C_{13}H_{17}Cl_2NO_2$(%):

| Element | Theory | Found |
|---------|--------|-------|
| C | 53.81 | 53.85 |
| H | 5.91 | 5.95 |
| Cl | 24.43 | 24.34 |

-continued
Anal. Calc'd for $C_{13}H_{17}Cl_2NO_2$(%):

| Element | Theory | Found |
|---------|--------|-------|
| N | 4.83 | 4.83 |

The product was identified as 2'-isobutoxy-N-(chloromethyl)-2-chloroacetanilide.

EXAMPLE 10

Following substantially the same procedure as above, but substituting as the starting amide, 6.2 g of 2'-(isopropoxyethoxy)-N-(methoxymethyl)-2-chloroacetanilide, and refluxing the mixture for 2.5 hours, there is obtained 5.3 g (84% yield) of an amber oil, b.p. 138° C. at 0.05 mm Hg (Kugelrohr); $N_D^{23.2}$ 1.5311.

Anal. Calc'd for $C_{15}H_{21}Cl_2NO_3$(%):

| Element | Theory | Found |
|---------|--------|-------|
| C | 53.90 | 53.79 |
| H | 6.33 | 6.36 |
| Cl | 21.21 | 21.15 |
| N | 4.19 | 4.15 |

The product was identified as 2'-(isopropoxyethoxy)-6'-methyl-N-(chloromethyl)-2-chloroacetanilide.

The process of this invention is of wide applicability as indicated in the above working embodiments. Substitution of thionyl bromide for thionyl chloride produces the analogous N-(bromomethyl) compound. Since the reactive site is in the halogen-ether cleavage process is at the N-methylene ether position, a wide variety of substituents may occupy the other non-acyl position in the amide. That is, in Formulae I and II herein, in addition to the R members exemplified above, other R members are within the purview of this invention. Thus, R may be hydrogen, aliphatic, cycloaliphatic, heterocyclic or aromatic members, including alkyl, alkenyl, alkynyl, cycloalkyl, alkylcycloalkyl, all preferably having up to 6 carbon atoms, N—, O—, or S-heterocyclic radicals, which members may be independently substituted with non-interfering radicals, e.g., alkyl, halogen, nitro, CF₃, alkoxy, polyalkoxy, alkoxyalkyl and the like. A subgenus of N-halomethyl compounds of particular interest is that wherein the R group is a phenyl radical substituted in one ortho position with a $C_{1-4}$ alkyl radical and in the other ortho position with a trifluoromethyl, $C_{1-4}$ alkyl or alkoxy or $C_{3-4}$ alkenyloxy radical. Exemplary of such compounds are the following:

N-(chloromethyl)-2'-methoxy-6'-methyl-2-chloroacetanilide
N-(chloromethyl)-2'-isopropoxy-6'-methyl-2-chloroacetanilide
N-(chloromethyl)-2'-isobutoxy-6'-methyl-2-chloroacetanilide
N-(chloromethyl)-2'-isobutoxy-6'-ethyl-2-chloroacetanilide
N-(chloromethyl)-2'-n-butoxy-6'-methyl-2-bromoacetanilide
N-(chloromethyl)-2',6'-dimethyl-2-bromoacetanilide
N-(chloromethyl)-2'-methyl-6'-ethyl-2-chloroacetanilide
N-(chloromethyl)-2'-(trifluoromethyl)-6'-methyl-2-chloroacetanilide
N-(chloromethyl)-2'-(trifluoromethyl)-6'-ethyl-2-chloroacetanilide N-(chloromethyl)-2'-(trifluoromethyl)-2-chloroacetanilide
N-(bromomethyl)-2'-methoxy-6'-methyl-2-chloroacetanilide
N-(bromomethyl)-2'-isopropoxy-6'-methyl-2-chloroacetanilide
N-(bromomethyl)-2'-isobutoxy-6'-methyl-2-chloroacetanilide
N-(bromomethyl)-2'-isobutoxy-6'-ethyl-2-chloroacetanilide
N-(bromomethyl)-2'-n-butoxy-6'-methyl-2-bromoacetanilide
N-(bromomethyl)-2',6'-dimethyl-2-bromoacetanilide
N-(bromomethyl)-2'-methyl-6'-ethyl-2-chloroacetanilide
N-(bromomethyl)-2'-(trifluoromethyl)-6'-methyl-2-chloroacetanilide
N-(bromomethyl)-2'-(trifluoromethyl)-6'-ethyl-2-chloroacetanilide
N-(bromomethyl)-2'-(trifluoromethyl)-2-chloroacetanilide Another subclass of compounds of interest is that wherein R in the above formulae is a $C_{5-7}$ 1-cycloalken-1-yl group, optionally substituted with one or more $C_{1-6}$ alkyl groups, e.g., N-(chloromethyl)-N-(2,5-dimethyl-1-cyclopenten-1-yl)-2-chloroacetamide and N-(chloromethyl)-N-(2,6-dimethyl-1-cyclohexen-1-yl)-2-chloroacetamide.

Yet another subclass of compounds according to Formula I herein is that wherein R is an acyclic 1-alken-1-yl radical having up to 10 carbon atoms as exemplified, e.g., by N-(chloromethyl)-N-[2-methyl--(1-methylethyl)-1-propenyl]-2-chloroacetamide and N-(chloromethyl)-N-(1,2-dimethyl-1-propenyl)-2-chloroacetamide.

In addition to N-(halomethyl)-2-haloacetamides, other acrylamides having non-halogen substituents in the 2- or α-position which may be prepared according to the process of this invention, include those wherein X in Formulae I and II above may be hydrogen, a $C_{1-6}$ alkyl or haloalkyl radical, a $C_{3-7}$ cycloalkyl radical, a phenyl or benzyl radical or any of said radicals optionally substituted with other radicals which are inert to a hydrogen halide, e.g., halogen, $NO_2$, $CF_3$, $C_{1-6}$ alkyl or alkoxy, phenyl, benzyl, etc.

As indicated above, the N-(halomethyl)acylamide compounds prepared according to the process of this invention are generally known compounds, some of which have herbicidal activity themselves. All of the N-halomethyl compounds disclosed above have utility as intermediate compounds (precursors) in the preparation of other compounds having herbicidal activity as disclosed, e.g., in the references cited above. Additionally, N-(halomethyl)-2-chloroacetamides prepared in accordance with the process of this invention are useful in the preparation of novel N-(azolylmethyl)-2-haloacetamides as set forth in this inventor's co-pending application Ser. No. 211609, filed Dec. 1, 1980. Examples 11-13 below are illustrative of the preparation of said novel 2-haloacetamides.

Example 11

To 1.4 g (0.0059 mol) of N-(chloromethyl)-N-[2-methyl-1-(1-methylethyl)-propen-1-yl]-2-chloroacetamide was added 0.8 g (0.012 mol) of pyrazole and the mixture heated in about 20 ml of toluene at 80°-90° C. for about 6-7 hours. The material was decanted, washed with 10% caustic then with water, stripped and recrystallized from methylcyclohexane to give 1.0 (63% yield) of white solid, m.p. 101.0°-101.5° C.

| Anal. calc'd for $C_{13}H_{20}ClN_3O$ (%): | | |
|---|---|---|
| Element | Theory | Found |
| C | 57.88 | 57.41 |
| H | 7.47 | 7.59 |
| N | 15.58 | 16.25 |

The product, structure confirmed by Nmr, was identified as N-[(2-methyl-1-(1-methylethyl)-1-propen-1-yl]-N-(1H-pyrazol-1-ylmethyl)-2-chloroacetamide.

Example 12

Pyrazol, 0.54 g (0.008 mol) and 0.8 g (0.0038 mol) of N-(chloromethyl)-N-(1,2-dimethyl-1-propen-1-yl)-2-chloroacetamide were mixed in toluene and heated at 90° C. On work-up as described in Example 11, 0.6 g (62% yield) of an amber oil was obtained.

| Anal. calc'd for $C_{11}H_{16}ClN_3O$ (%): | | |
|---|---|---|
| Element | Theory | Found |
| C | 54.66 | 54.71 |
| H | 6.67 | 6.80 |
| N | 17.38 | 17.51 |

The product, confirmed by Nmr, was identified as N-(1,2-dimethyl-1-propen-1-yl)-N-(1H-pyrazol-1-ylmethyl)-2-chloroacetamide.

Example 13

To 8.9 g (0.036 mol) of N-(chloromethyl)-N-(2,6-dimethyl-1-cyclohexen-1-yl)-2-chloroacetamide dissolved in toluene was added 4.9 g (0.072 mol) of pyrazole; this mixture was heated to 90° C. with stirring for 7 hours. The following day, the toluene solution was decanted, washed twice with water, then vacuum distilled to remove the solvent and traces of moisture. The residue was 9.0 g of an oil which crystallized on standing. A sample of the product was recrystallized from a heptane/methylcyclohexane solvent to give a solid product, m.p. 83°-84° C., in 89% yield.

| Anal. calc'd for $C_{14}H_{20}ClN_3O$ (%): | | |
|---|---|---|
| Element | Theory | Found |
| C | 59.67 | 59.64 |
| H | 7.15 | 7.17 |
| N | 14.91 | 14.96 |

The product was identified as N-(2,6-dimethyl-1-cyclohexen-1-yl)-N-(1H-pyrazol-1-ylmethyl)-2-chloroacetamide.

Example 14

This example describes the use of an N-(halomethyl)-substituted-2-haloacetanilide to prepare other novel N-heteromethyl-2-haloacetanilides as disclosed and claimed in this inventor's co-pending application, Ser. No. 133,763, filed Mar. 25, 1980.

N-(chloromethyl)-2'-methoxy-6'-methyl-2-chloroacetanilide 3.6 g (0.0137 mol), in 100 ml of $CH_2Cl_2$ were mixed with benzothiazolin-2-one, 2.2 g (0.0145 mol) and 1.0 benzyl triethyl ammonium bromide. To this mixture with stirring was added 30 ml of 50% caustic; the mixture was allowed to react for about three hours. On work-up 5.8 g crude product was isolated, then recrystallized from isopropanol to a light buff-colored solid, m.p. 120°–121° C.

| Anal. calc'd for $C_{18}H_{17}ClN_2O_3S(\%)$: | | |
|---|---|---|
| Element | Theory | Found |
| C | 57.37 | 56.89 |
| H | 4.55 | 4.51 |
| N | 7.43 | 7.34 |

The product was identified as N-(2'-methoxy-6'-methyl)-N-[(2-oxo-3(2H)-benzothiazolyl)methyl]-2-chloroacetanilide.

It will be appreciated by those skilled in the art that the process of this invention may be modified in non-inventive modes by those skilled in the art having particular reference to the nature and ratio of reactants, particular species within the defined genus of reactants, catalysts, solvents, reaction temperatures, times, pressures, etc.

I claim:

1. Process for preparing compounds of Formula I

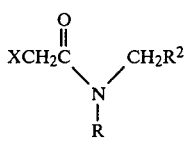

which comprises reacting a compound of Formula II

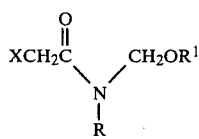

with thionyl chloride or thionyl bromide in the presence of a Lewis Acid catalyst where in the above formulae X is hydrogen, halogen, a $C_{1-6}$ alkyl or haloalkyl radical, a $C_{3-7}$ cycloalkyl radical, a phenyl or benzyl radical or any of said radicals substituted with halogen, $NO_2$, $CF_3$, $C_{1-6}$ alkyl or alkoxy, phenyl or benzyl;

R is a $C_{1-20}$ alkkyl radical, an acyclic 1-alken-1-yl radical having up to 10 carbon atoms, a cycloalkyl or 1-cycloalken-1-yl radical having up to 7 carbon atoms, a pheny radical or said cycloalkyl, 1-cycloalken-1-yl or phenyl radicals substituted with one or more $C_{1-6}$ alkyl, alkoxy or alkoxyalkyl, $C_{2-4}$ alkenyl or $C_{3-4}$ alkenyloxy, $NO_2$ or trifluoromethyl radicals or halogen;

$R^1$ is a hydrocarbyl radical having up to 10 carbon atoms or such radical substituted with halogen or $C_{1-8}$ alkoxy or alkoxyalkyl groups and $R^2$ is a chloro or bromo atom.

2. Process according to claim 1 wherein said reaction is conducted at temperatures within the range of about 0° to 100° C.

3. Process according to claim 2 wherein said temperature is reflux temperature.

4. Process according to claim 3 wherein said Lewis Acid catalyst is boron trifluoride etherate.

5. Process according to claim 4 wherein X is a chloro atom.

6. Process according to claim 5 wherein R is an acyclic 1-alken-1-yl radical having up to 10 carbon atoms.

7. Process according to claim 6 wherein said compound of Formula I is N-(chloromethyl)-N-[2-methyl-1-(1-methylethyl)-1-propenyl]-2-chloroacetamide.

8. Process according to claim 6 wherein said compound of Formula I is N-(chloromethyl)-N-(1,2-dimethyl-1-propenyl)-2-chloroacetamide.

9. Process according to claim 5 wherein R is a $C_{5-7}$ 1-cycloalken-1-yl radical, optionally substituted with one or more $C_{1-6}$ alkyl radicals.

10. Process according to claim 9 wherein said compound of Formula I is N-(chloromethyl)-N-(2,6-dimethyl-1-cyclohexen-1-yl)-2-chloroacetamide.

11. Process according to claim 5 wherein R is a phenyl radical, optionally substituted with one or more $C_{1-6}$ alkyl, alkoxy or alkoxyalkyl, $C_{2-4}$ alkenyl or $C_{3-4}$ alkenyloxy or trifluoromethyl radicals or halogen.

12. Process according to claim 11 wherein R is a phenyl radical substituted in both ortho positions with $C_{1-6}$ alkyl radicals.

13. Process according to claim 12 wherein said compound of Formula I is N-(chloromethyl)-2',6'-diethyl-2-chloroacetanilide.

14. Process according to claim 12 wherein said compound of Formula I is N-(chloromethyl)-2'-methyl-6'-ethyl-2-chloroacetanilide.

15. Process according to claim 11 wherein R is a phenyl radical substituted in one ortho position with a $C_{1-6}$ alkyl radical and in the other ortho position with a trifluoromethyl radical.

16. Process according to claim 15 wherein said compound of Formula I is N-(chloromethyl)-2'-(trifluoromethyl)-6'-methyl-2-chloroacetanilide.

17. Process according to claim 15 wherein said compound of Formula I is N-(chloromethyl)-2'-(trifluoromethyl)-6'-ethyl-2-chloroacetanilide.

18. Process according to claim 11 wherein R is a phenyl radical substituted in one ortho position with a $C_{1-6}$ alkyl radical and in the other ortho position with a $C_{1-6}$ alkoxy or $C_{3-4}$ alkenyloxy radical.

19. Process according to claim 18 wherein said alkyl radical is methyl or ethyl.

20. Process according to claim 19 wherein said alkoxy radical is a methoxy or $C_3$ or $C_4$ alkoxy radical.

21. Process according to claim 20 wherein said compound of Formula I is N-(chloromethyl)-2'-methoxy-6'-methyl-2-chloroacetanilide.

22. Process according to claim 20 wherein said compound of Formula I is N-(chloromethyl)-2'-isopropoxy-6'-methyl-2-chloroacetanilide.

23. Process according to claim 20 wherein said compound of Formula I is N-(chloromethyl)-2'-isobutoxy-6'-methyl-2-chloroacetanilide.

24. Process according to claim 20 wherein said compound of Formula I is N-(chloromethyl)-2'-isobutoxy-6'-ethyl-2-chloroacetanilide.

25. Process according to claim 20 wherein said compound of Formula I is N-(chloromethyl)-2'-n-butoxy-6'-ethyl-2-chloroacetanilide.

26. Process according to claim 19 wherein said other ortho position is occupied by a $C_{3-4}$ alkenyloxy radical.

27. Process according to claim 26 wherein said compound of Formula I is N-(chloromethyl)-2'-(1-propen-3-yloxy)-6'-methyl-2-chloroacetanilide.

28. Process according to claim 9 wherein said compound of Formula I is N-(chloromethyl)-N-(2,5-dimethyl-1-cyclopenten-1-yl)-2-chloroacetamide.

* * * * *